(12) United States Patent
Ponshock et al.

(10) Patent No.: US 10,024,772 B1
(45) Date of Patent: Jul. 17, 2018

(54) DEVICE AND METHOD FOR APPLYING INTERNAL PRESSURE TO A HOLLOW CYLINDER

(71) Applicant: The United States of America, as represented by the Secretary of the Navy, Washington, DC (US)

(72) Inventors: Timothy David Ponshock, Monterey, CA (US); Young Wuk Kwon, Monterey, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 352 days.

(21) Appl. No.: 15/137,090

(22) Filed: Apr. 25, 2016

Related U.S. Application Data

(60) Provisional application No. 62/163,792, filed on May 19, 2015, provisional application No. 62/262,243, filed on Dec. 2, 2015.

(51) Int. Cl.
*G01N 3/08* (2006.01)
(52) U.S. Cl.
CPC ...................... *G01N 3/08* (2013.01)
(58) Field of Classification Search
CPC ....................................................... G01N 3/08
USPC .................................................... 73/818, 803
See application file for complete search history.

(56) References Cited

U.S. PATENT DOCUMENTS

| | | | |
|---|---|---|---|
| 6,595,068 B2* | 7/2003 | Brovold ................... | G01N 3/10 73/803 |
| 8,353,217 B2* | 1/2013 | Rigaud ..................... | G01N 3/12 73/760 |
| 2001/0037687 A1* | 11/2001 | Brovold ................... | G01N 3/10 73/826 |
| 2014/0014561 A1* | 1/2014 | Tzeng ..................... | B01D 35/06 210/85 |

* cited by examiner

*Primary Examiner* — Lisa Caputo
*Assistant Examiner* — Jamel Williams
(74) *Attorney, Agent, or Firm* — Naval Postgraduate School; Lisa A. Norris

(57) ABSTRACT

A device and method for applying an internal pressure and resultant hoop stress to a hollow cylindrical object, such as a test cylinder, utilizing an expandable cylinder and upper and lower conically shaped rams. The device is inserted into a test cylinder, and when a compressive force is applied to the upper and lower conically shaped rams, the rams move vertically into upper and lower conically shaped cavities of the expandable cylinder. The sloped inner surfaces of the conically shaped upper and lower cavities convert the vertical motion into an outward radial motion, applying an internal pressure and resultant hoop stress to the cylindrical object.

20 Claims, 16 Drawing Sheets
(2 of 16 Drawing Sheet(s) Filed in Color)

DEVICE AND METHOD FOR APPLYING INTERNAL PRESSURE TO A HOLLOW CYLINDER

CROSS-REFERENCE TO RELATED APPLICATIONS

This application claims the benefit of U.S. Provisional Application No. 62/163,792 filed May 19, 2015, and U.S. Provisional Application No. 62/262,243 filed Dec. 2, 2015, each of which is hereby incorporated in its entirety by reference.

BACKGROUND OF THE INVENTION

1. Field of the Invention

The present invention relates generally to devices and methods for applying an internal pressure to a hollow cylindrical shape.

2. Description of the Related Art

Application of an internal pressure and the resultant hoop stress to a hollow cylinder may be employed for various research, design, and/or testing requirements. Some prior art systems utilized a direct method for applying this pressure by filling the cylinder with an incompressible fluid, capping the ends of the cylinder, and using an external source to pressurize the fluid. This method is undesirable for several reasons. First, capping the ends results in end effects that introduce unwanted constraints to the cylinders as well as being difficult to accomplish with cylindrical structures. Secondly, high pressures, on the order of 10,000 psi, can be generated during testing, and such a high pressure is dangerous to personnel and equipment if the tested cylinder fails. Finally, these prior art systems required additional external equipment, such as a pump and lines, that added to the cost and complexity of the testing.

For example, some prior art systems made use of a bladder pressurized either indirectly by an external pump or directly by a piston pressing on the bladder using a compression testing machine. For example, U.S. Pat. No. 6,595,068 B2 describes a prior art device that uses an external compressor to pressurize an inflatable membrane to apply a hoop stress to a test cylinder. U.S. Pat. No. 8,353,217 B2 describes a device which uses a piston in conjunction with a compression testing machine to pressurize a bladder around which a test cylinder is placed.

While the above prior art systems provide a means for applying a hoop stress without capping the ends of the cylinder, they still required a pressurized fluid which adds complexity to their design and use. Furthermore, these prior art systems involve more complicated equipment resulting in a more expensive and difficult-to-manufacture device.

SUMMARY OF THE INVENTION

Embodiments in accordance with the invention include a device and method for applying an internal pressure and resultant hoop stress to a hollow cylindrical shape. In accordance with one embodiment, a device for applying internal pressure to a hollow cylindrical object includes: an upper conical ram having a first guide hole centrally formed in a first facing surface; a lower conical ram having a second guide hole centrally formed in a second facing surface, wherein the second guide hole and the first guide hole are aligned to allow a guide rod to be positioned within both the first guide hole and the second guide hole; an expandable cylinder, the expandable cylinder having a 360 degree cylindrical exterior surface, an internal conical upper cavity shaped to receive at least a portion of the upper conical ram and an internal conical lower cavity shaped to receive at least a portion of the lower conical ram; and a guide rod positioned within at least a portion of the first guide hole and the second guide hole, the guide rod for aligning the upper conical ram and the lower conical ram. In one embodiment, the expandable cylinder includes a plurality of wedges, each wedge having an exterior surface that forms a portion of the 360 degree exterior surface of the expandable cylinder and having an interior surface shaped to form a portion of the internal conical upper cavity and a portion of the internal conical lower cavity of the expandable cylinder. In some embodiments, the device further includes a shim.

In accordance with one embodiment, a method for applying an internal pressure to a hollow cylindrical object includes: obtaining a test cylinder; inserting an expandable cylinder into the test cylinder, the expandable cylinder having a 360 degree cylindrical exterior surface, an internal conical upper cavity shaped to receive at least a portion of an upper conical ram and an internal conical lower cavity shaped to receive at least a portion of a lower conical ram; inserting the lower conical ram from below the test cylinder at least partially into the lower cavity of the expandable cylinder, the lower conical ram having a second guide hole centrally formed on a second facing surface; inserting a guide rod from above the test cylinder into the second guide hole; inserting the upper conical ram from above the test cylinder at least partially into the upper cavity of the expandable cylinder, the upper conical ram having a first guide hole centrally formed on a first facing surface, wherein the first guide hole is aligned over the guide rod such that the guide rod passes into the first guide hole, and further wherein the first facing surface and the second facing surface are separated by a gap having a distance, d; applying a measured compressive force to the lower conical ram and the upper conical ram to cause the lower conical ram and the upper conical ram to move vertically toward a midline of the expandable cylinder and create an outward radial motion which applies an internal pressure and resultant hoop strain on the test cylinder; and determining a hoop stress of the test cylinder based on at least the hoop strain.

Embodiments in accordance with the invention are best understood by reference to the following detailed description when read in conjunction with the accompanying drawings

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
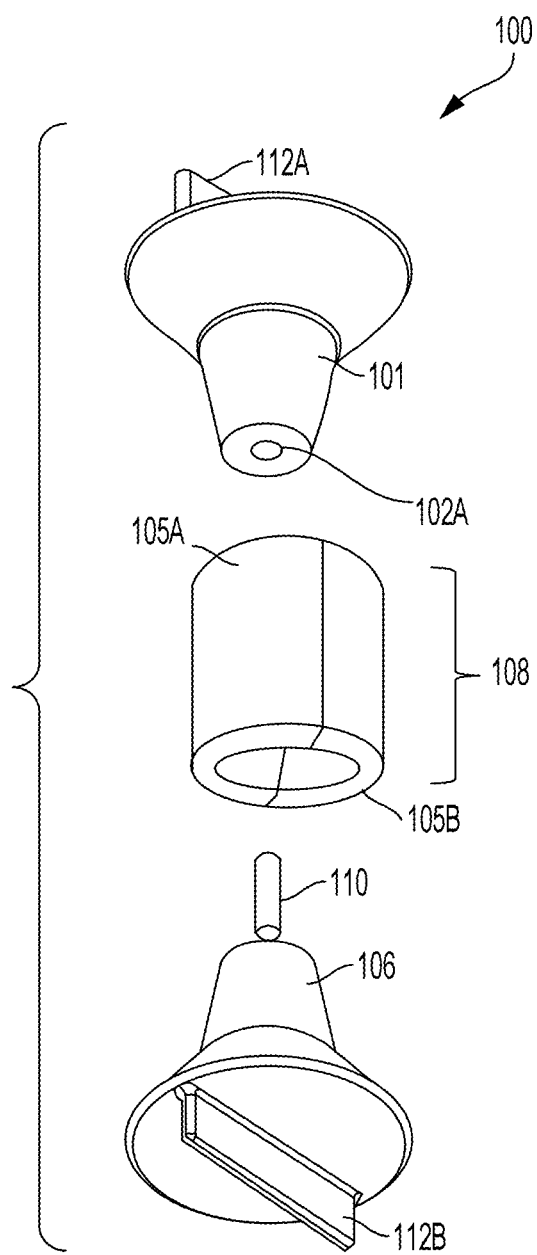
FIG. 1 illustrates an exploded perspective view drawing of a device for applying an internal pressure to a hollow cylindrical shape in accordance with one embodiment of the invention.
Figure 2:
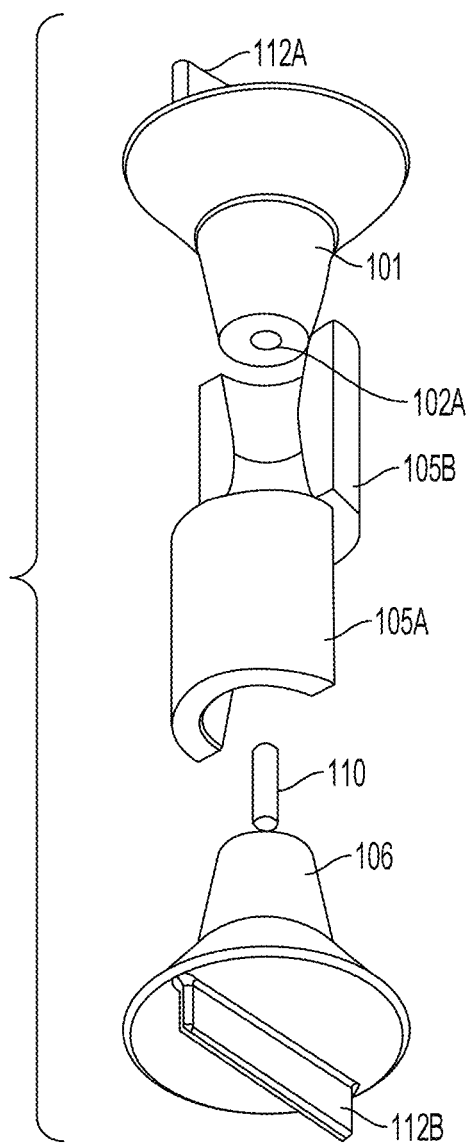
FIG. 2 illustrates an exploded perspective view drawing of the device of FIG. 1 in which the wedges of the expandable cylinder are separated in accordance with one embodiment of the invention.
Figure 3:
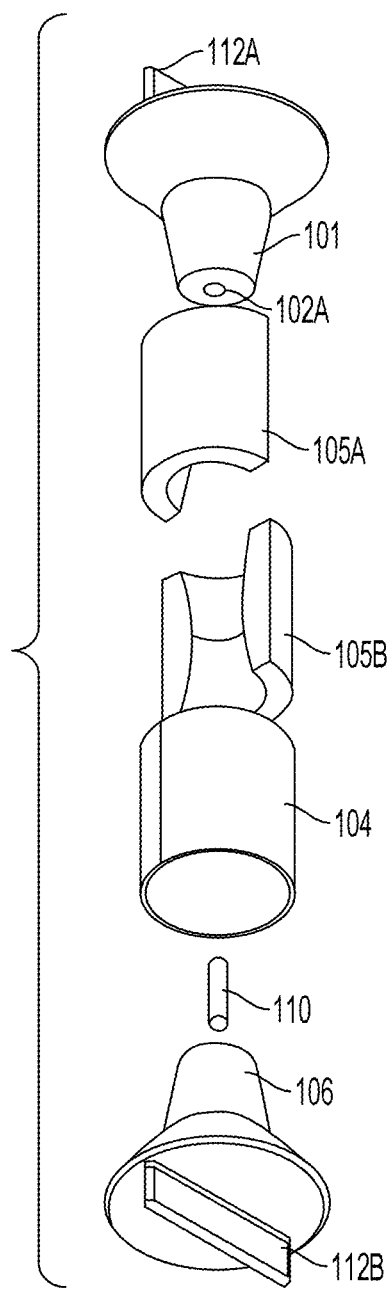
FIG. 3 illustrates an exploded perspective view drawing of the device of FIG. 1 including an optional shim in accordance with one embodiment of the invention.
Figure 4:
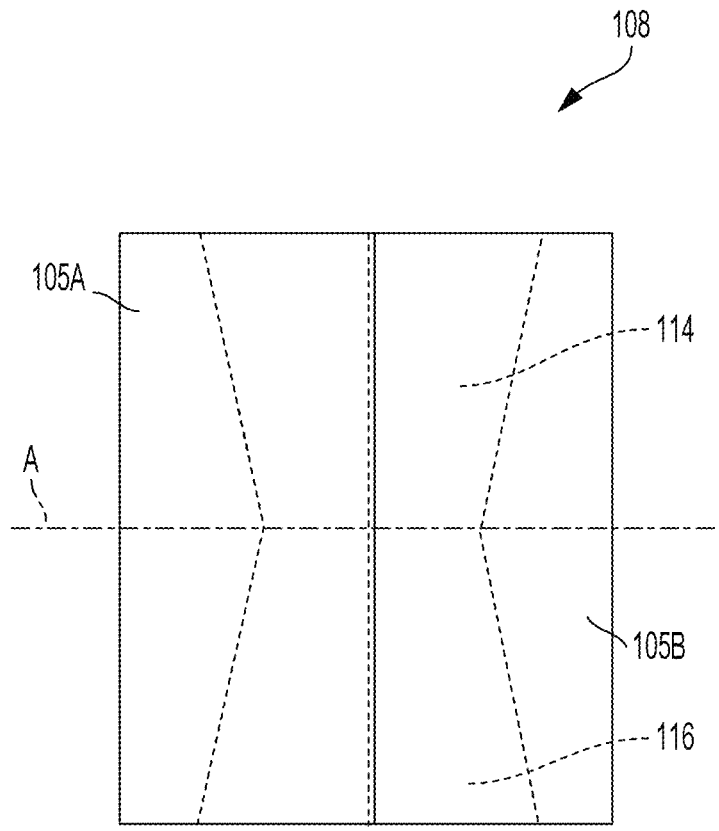
FIG. 4 illustrates a side view drawing of the expandable cylinder of FIG. 1 showing the upper and lower internal cavities in accordance with one embodiment of the invention

Embodiments in accordance with the invention are further described herein with reference to the drawings.

DETAILED DESCRIPTION OF THE INVENTION

Embodiments in accordance with the invention include a device and method for applying an internal pressure and resultant hoop stress to a hollow cylindrical shape, such as a test cylinder. Embodiments in accordance with the invention provide a simple and mechanical device that allows application of an internal pressure and resultant hoop stress to hollow cylinders of various sizes when used with a standard compression testing machine and eliminates the danger inherently present when dealing with high pressure fluids.

Referring now to FIGS. 1 through 9 together, in one embodiment, a device 100 for applying internal pressure to a hollow cylinder includes an upper conical ram 101, herein also referred to as a first conical ram, and a lower conical ram 106, herein also referred to as a second conical ram, that are each conically shaped to fit and move within corresponding upper and lower conically shaped interior cavities formed in an expandable cylinder 108. In one embodiment, expandable cylinder 108 is composed of two wedges 105A and 105B, herein also referred to as a first wedge, and a second wedge, respectively.

When placed together each wedge 105A, 105B forms a corresponding half of expandable cylinder 108. In one embodiment, expandable cylinder 108 has a 360 degree external surface with cylindrical cross section, and has an internal upper cavity 114 and an internal lower cavity 116 which meet at a midline A. Each wedge 105B, 105B has a 180 degree exterior surface and has a shaped interior surface formed such that, when placed together, each wedge 105A, 105B forms a corresponding half of upper cavity 114 and lower cavity 116.

Figure 5:
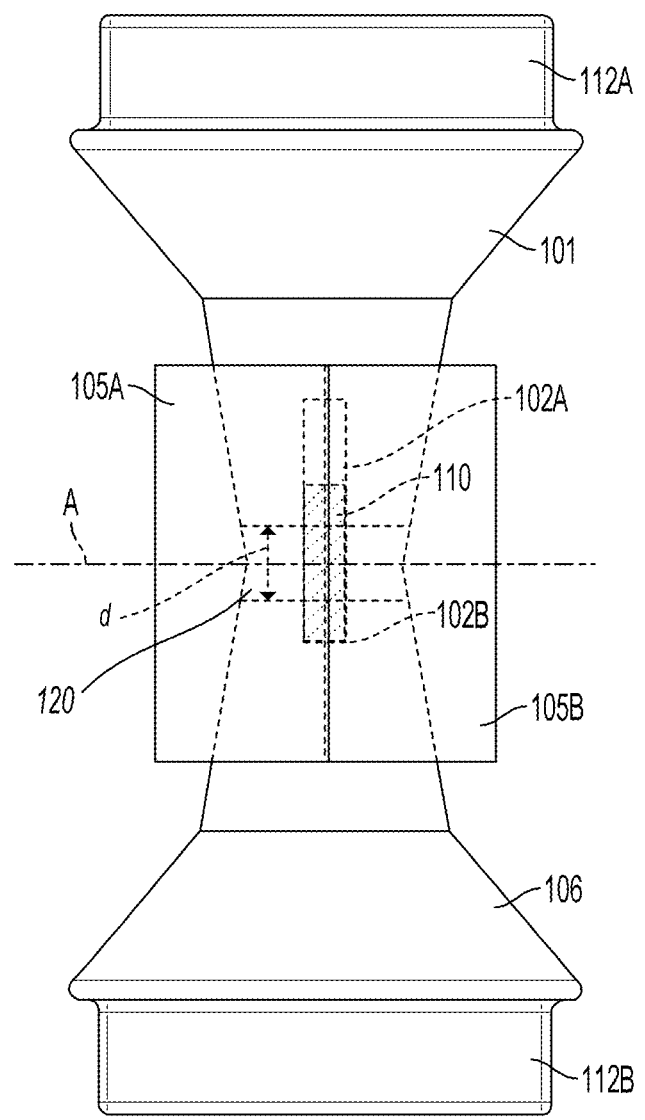
FIG. 5 illustrates a side view drawing of the device of FIG. 1 in accordance with one embodiment of the invention.
Figure 6:
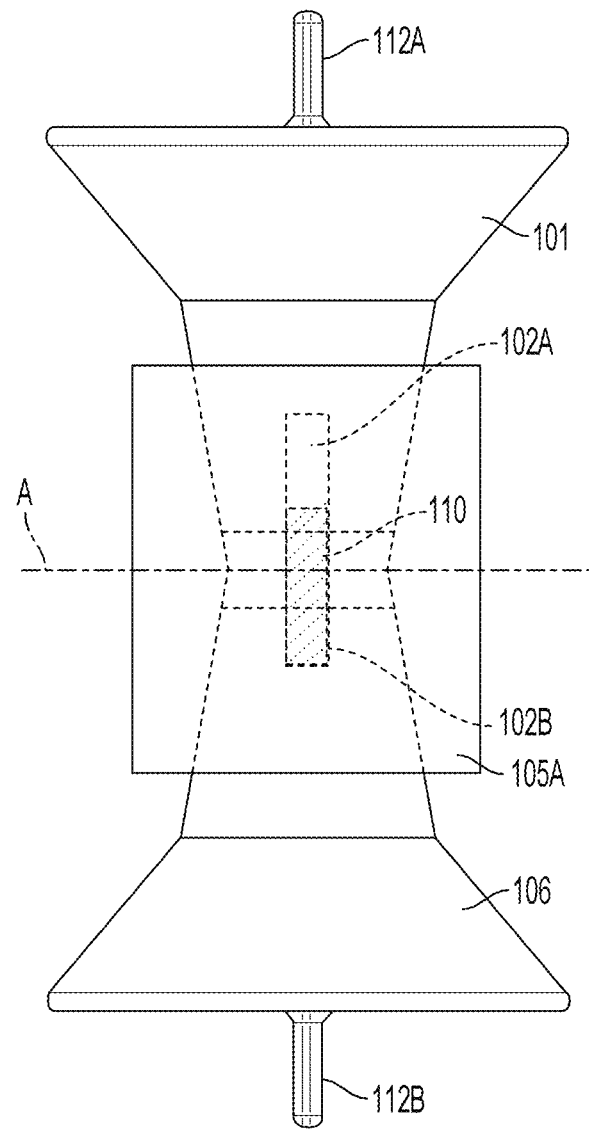
FIG. 6 illustrates a front view drawing of the device of FIG. 1 in accordance with one embodiment of the invention.
Figure 7:
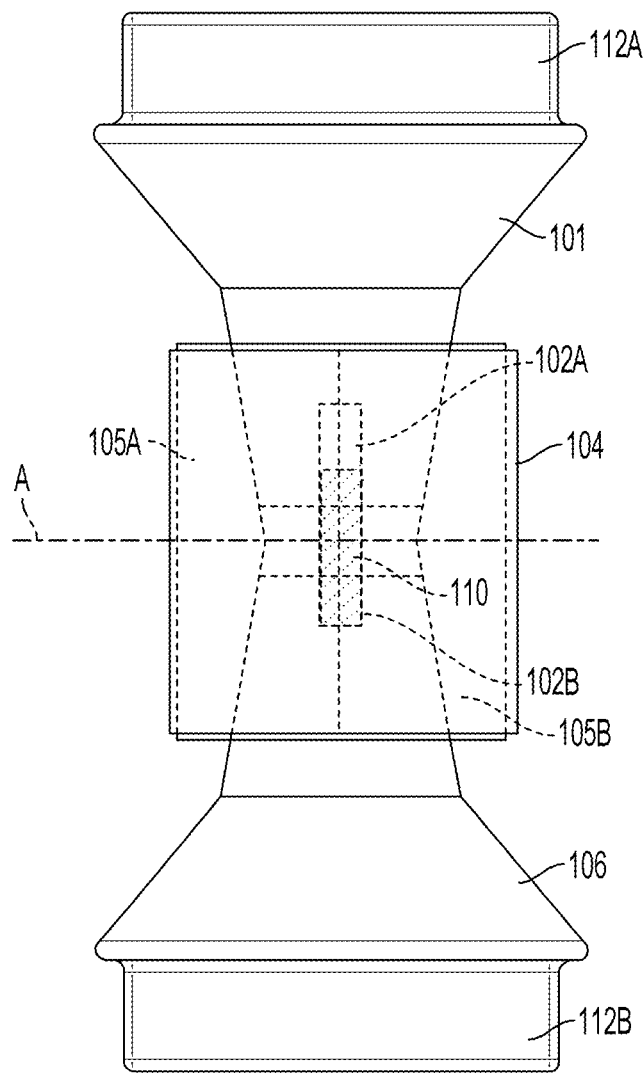
FIG. 7 illustrates a side view drawing of the device of FIG. 1 including an optional shim in accordance with one embodiment of the invention

In one embodiment upper cavity 114 and lower cavity 116 are conically shaped. In one embodiment, upper cavity 114 and lower cavity 116 each have a graduated conical shape with cylindrical cross section that decreases in diameter toward midline A. As illustrated in FIG. 5, the slopes of the conical shape of upper cavity 114 and lower cavity 116 are formed such that, when wedges 105A, 105B are placed together, when upper conical ram 101 and lower conical ram 106 are inserted into upper cavity 114 and lower cavity 116, a gap 120 having a distance d is formed between the facing surface of upper conical ram 101 and the facing surface of lower conical ram 106. Gap 120 allows space for vertical movement of upper conical ram 101 and lower conical ram 106 toward midline A of expandable cylinder 108 when a compressive force is applied. The vertical movement into gap 120 results in an outward expansion of wedges 105A, 105B, i.e., circumferential expansion of expandable cylinder 108.

Each conical ram 101, 106 is connectable to a compression testing machine, such as a uniaxial compression testing machine, not shown. In one embodiment upper conical ram 101 includes a tab 112A and lower conical ram 106 includes a tab 112B that allow conical rams 101, 106 to be inserted into and connected with a compression testing machine. It is well known in the art that various objects and devices may be connected to compression testing machines via various connections, such as electrical and mechanical connections, not shown.

In one embodiment, a first guide hole 102A in a facing surface of upper conical ram 101 and a second guide hole 102B in a facing surface of lower conical ram 106 are formed to receive a guide rod 110 that provides axial alignment of upper conical ram 101 and lower conical ram 106. First guide hole 102A is centrally located and formed in the facing surface of upper conical ram 101, and second guide hole 102B is centrally located and formed in the facing surface of lower conical ram 106. Second guide hole 102B is formed a depth deep enough to allow a portion of guide rod 110 to be inserted into lower conical ram 106 and the remaining portion of guide rod 110 to extend out from the facing surface of lower conical ram 106. First guide hole 102A is formed a depth deep enough to allow the remaining portion of guide rod 110 that extends from second guide hole 102 to be inserted into upper conical ram 101 when facing surfaces of upper conical ram 101 and lower conical ram 106 meet at midline A.

In one embodiment, optionally, a shim 104, which can be formed of various thicknesses, can be placed around the outer surfaces of expansion cylinder 108 to properly size, i.e., fit, expansion cylinder 108 within an interior void of a hollow cylinder to be tested, also referred to herein as a test cylinder. In one embodiment, shim 104 is a hollow cylindrical shape with a longitudinal gap which allows shim 104 to be sized between expansion cylinder 108 and different interior diameters of test cylinders. In other embodiments, shim 104 can be formed without the gap; however, multiple shims may then be needed to size expansion cylinder 108 to test cylinders having different diameter interior voids. In one embodiment, one or more shims 104 should be inserted until all wedges that form expansion cylinder 108, e.g., wedges 105A, 105B, are in contact with neighboring wedges, so that gap 120 is initially present.

Figure 8:
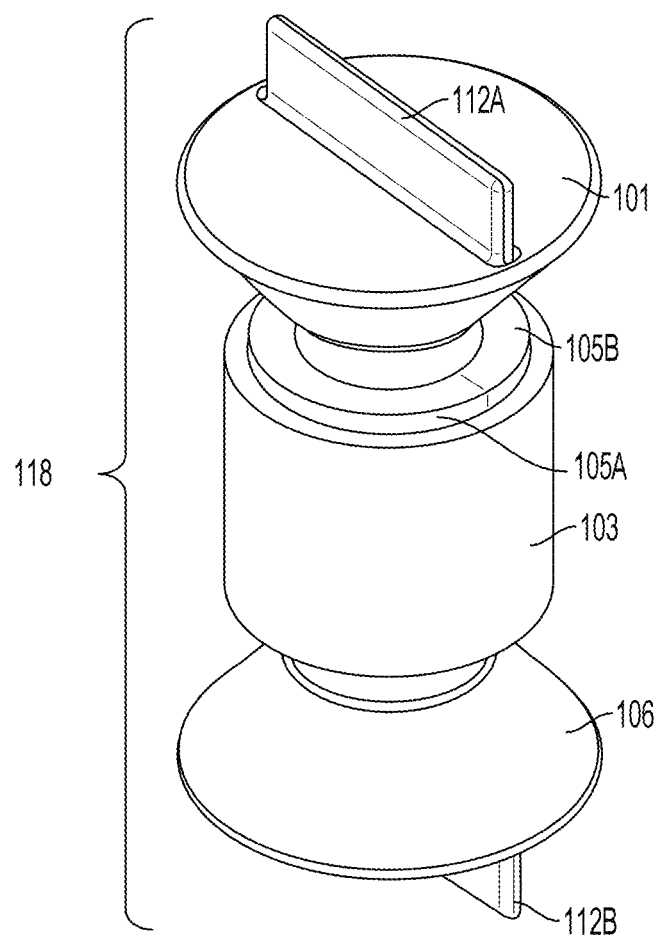
FIG. 8 illustrates a perspective view drawing of the device of FIG. 1 assembled with a test cylinder to form a test assembly in accordance with one embodiment of the invention.
Figure 9:
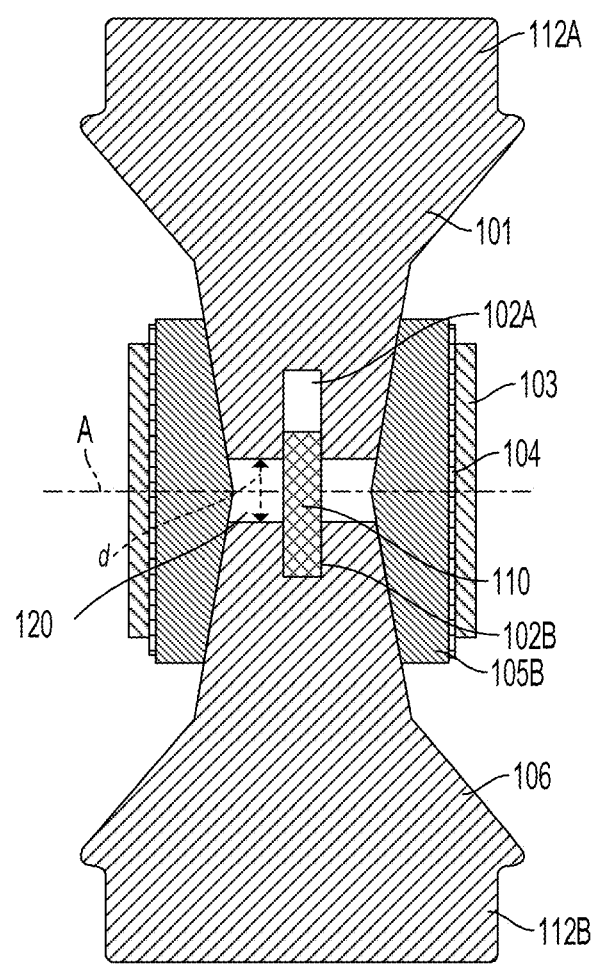
FIG. 9 illustrates a cut-away front view drawing of the device of FIG. 1 assembled with a test cylinder and including an optional shim to form a test assembly in accordance with one embodiment of the invention.

Referring now more particularly to FIGS. 8 and 9, when device 100 is assembled with a test cylinder 103, and optionally with shim 104, a test assembly 118 is formed. FIG. 8 shows a test assembly without shim 104, and FIG. 9 shows a test assembly including shim 104. As shown in FIG. 9, when initially assembled, the facing surface of lower conical ram 106 and the facing surface of upper conical ram 101 are separated by gap 120 having distance d. Gap 120 allows lower conical ram 106 and upper conical ram 101 to move toward midline A when a compressive force is applied. The vertical movement into gap 120 results in an outward expansion of wedges 105A, 105B with resultant internal pressure applied to cylinder 103.

Figure 10:
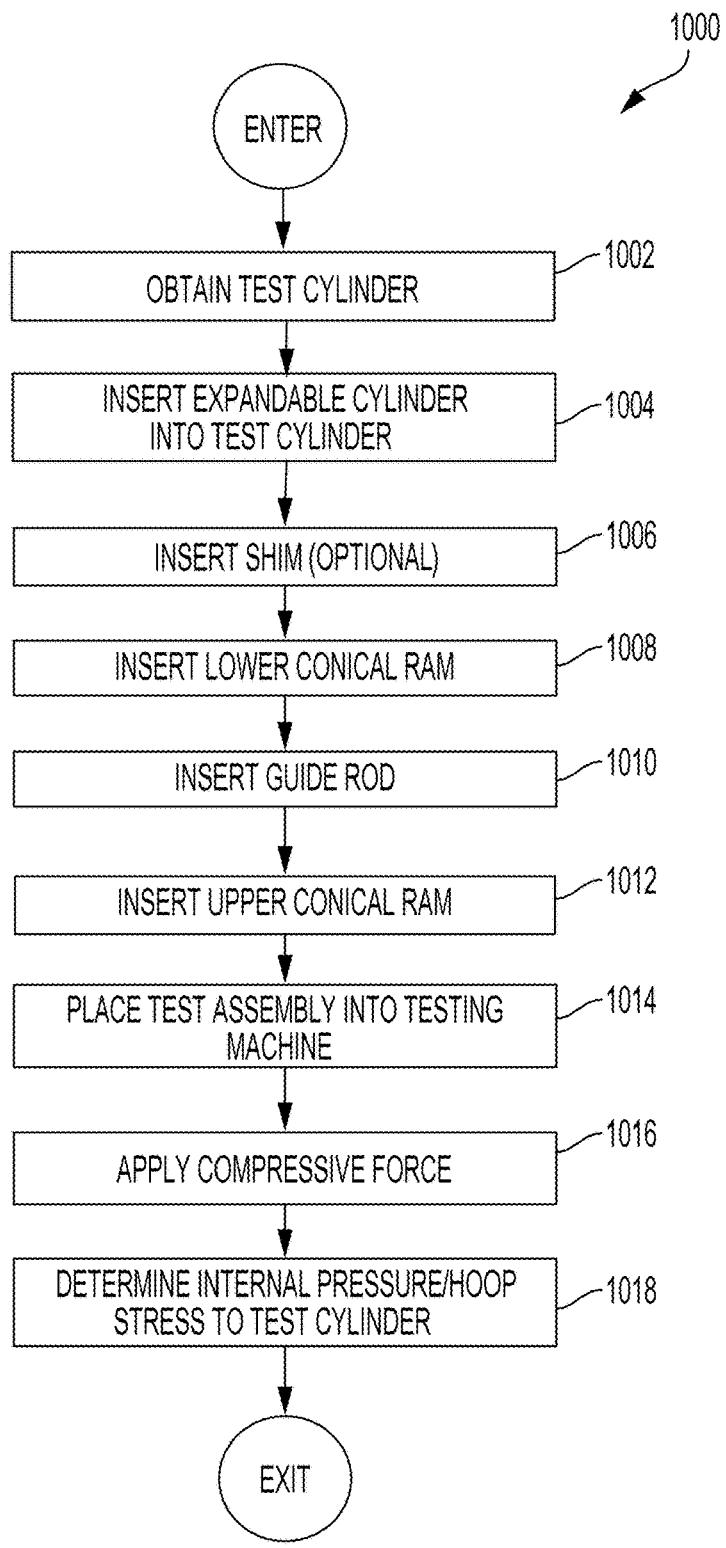
FIG. 10 illustrates a process flow drawing of a method for applying an internal pressure to a hollow cylindrical shape to determine a resultant hoop stress in accordance with one embodiment of the invention.
Figure 11:
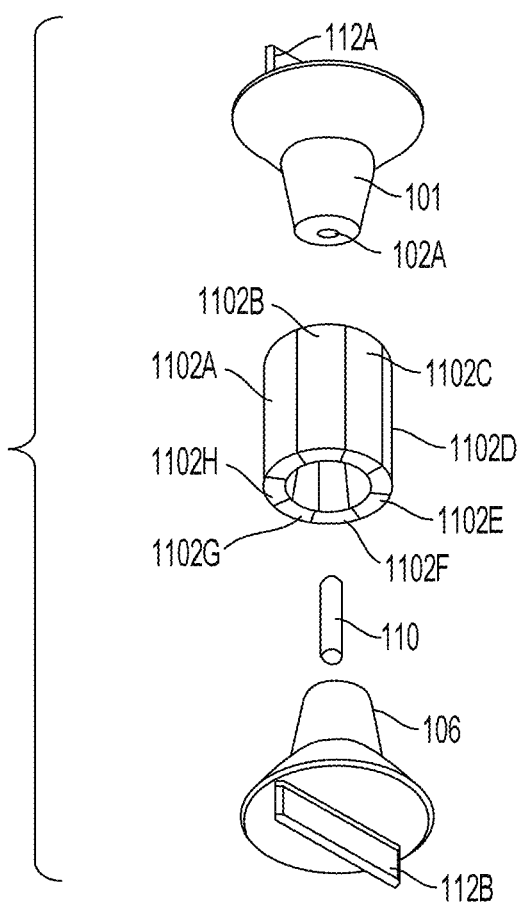
FIG. 11 illustrates an exploded perspective view drawing of a device for applying an internal pressure to a hollow cylindrical shape including an optional shim in accordance with another embodiment of the invention
Figure 12:
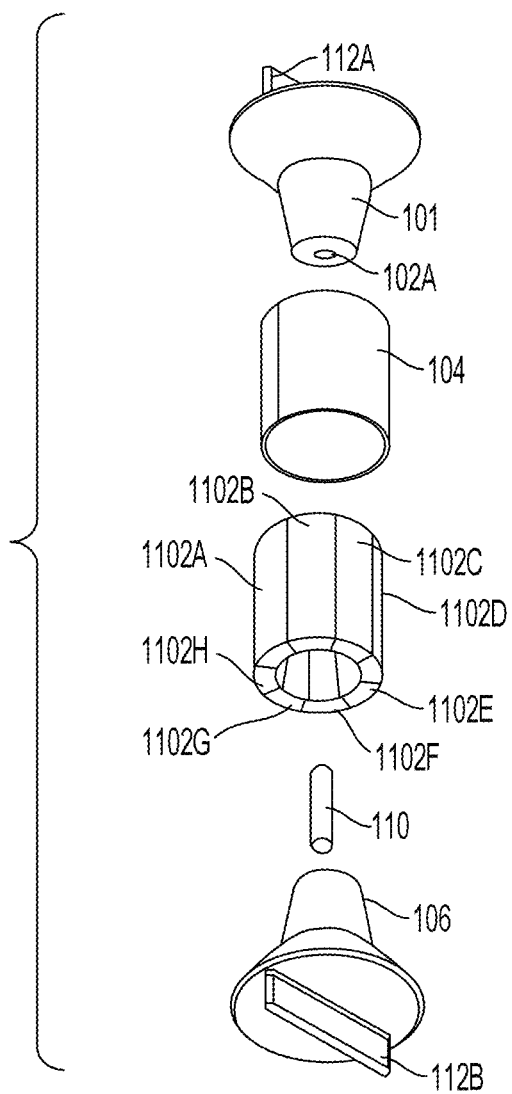
FIG. 12 illustrates an exploded perspective view drawing of the device of FIG. 11 including an optional shim in accordance with another embodiment of the invention
Figure 13:
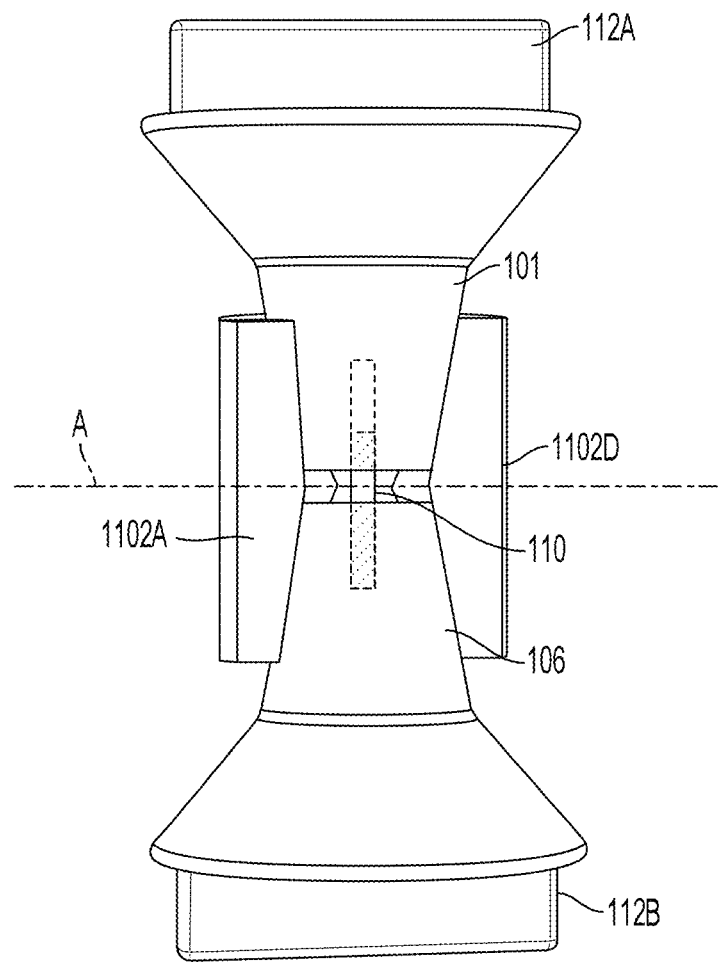
FIG. 13 illustrates a partial cutaway view drawing of the device of FIG. 11 in accordance with another embodiment of the invention.
Figure 14:
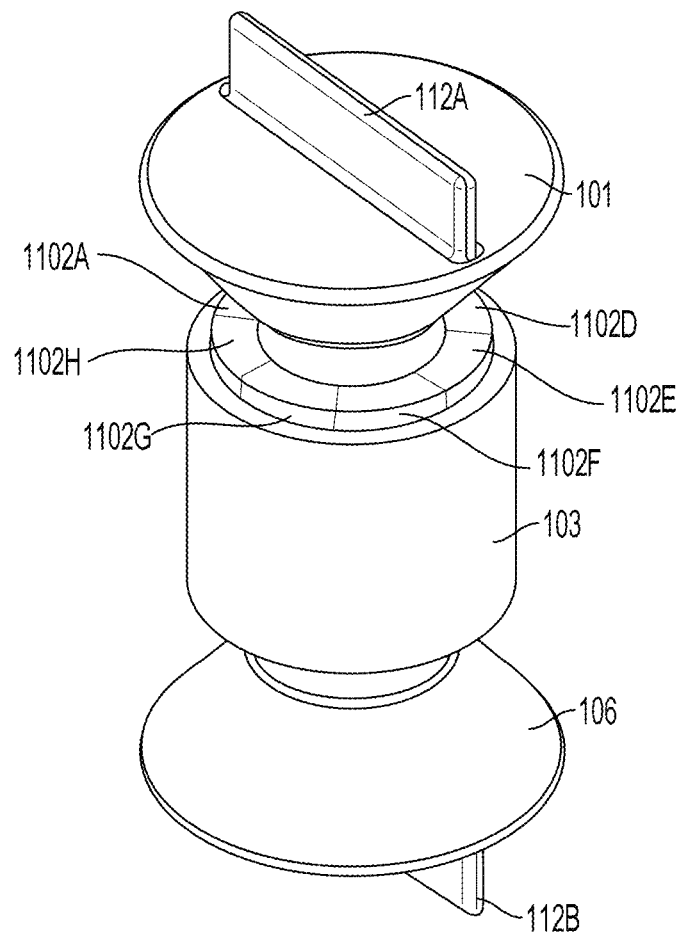
FIG. 14 illustrates a perspective view drawing of the device of FIG. 11 assembled with a test cylinder in accordance with one embodiment of the invention.

Referring now to FIG. 10 together with FIGS. 1-9, in one embodiment, a method 1000 for applying internal pressure to a hollow cylinder, such as a test cylinder, utilizing device 100 is described. In operation 1002 a test cylinder, such as test cylinder 103, is obtained. In operation 1004, expandable cylinder 108 is placed inside test cylinder 103. More specifically, wedges 105A, 105B which form expandable cylinder 108 are placed inside test cylinder 103. Optionally, in operation 1006, shim 104 is placed inside test cylinder 103 between the exterior surface of expandable cylinder 108 and the interior surface of test cylinder 103. In the present example, shim 104 is placed inside test cylinder 103 between the exterior surfaces of wedges 105A, 105B and the interior surface of test cylinder 103.

In operation 1008, lower conical ram 106 is inserted into lower cavity 116 from below expandable cylinder 108 and is in contact with at least a portion of the inner surfaces of wedges 105A, 105B which form lower cavity 116. In operation 1010, guide rod 110 is inserted from above and through the interior hollow of test cylinder 103 and into guide hole 102B of lower conical ram 106. In operation 1012, upper conical ram 101 is inserted into upper cavity 114 from above expandable cylinder 108 and is contact with at least a portion of the inner surfaces of wedges 105A, 105B which form upper cavity 114. Upper conical ram 101 is aligned such that guide rod 110 enters guide hole 102A of upper conical ram 101.

As earlier described, when initially assembled, the facing surface of lower conical ram 106 and the facing surface of upper conical ram 101 are separated by a gap 120 having a distance d (see FIG. 9). When device 100 is assembled with test cylinder 103, and optionally with shim 104, test assembly 118 is formed.

In operation 1014, test assembly 118 is placed into a compression testing machine, such as a uniaxial compression testing machine. Compression testing machines, including uniaxial compression testing machines, are well known to those of skill in the art. In one embodiment, tabs 112A, 112B are held by clamps on the compression testing machine and allow the compression testing machine to apply a compressive force on upper conical ram 101 and lower conical ram 106. In one embodiment, strain gauges are attached to test cylinder 103 to provide strain gauge measurements, such as hoop strain.

In operation 1016, the compression testing machine is initiated and applies a measured compressive force on upper conical ram 101 and lower conical ram 106. Application of the compressive force moves upper conical ram 101 down in upper cavity 114 and vertically toward midline A, and moves lower conical ram 106 up in lower cavity 116 and vertically toward midline A. This vertical movement reduces distance d of gap 120. The sloped inner surfaces of upper cavity 114 and lower cavity 116 convert the vertical motion into an outward radial motion forcing wedges 105A, 105B apart and applying an internal pressure and resultant hoop strain to test cylinder 103. The hoop strain on test cylinder 103 is measured by the strain gauges attached to test cylinder 103. In operation 1018, the compressive pressure and strain gauge measurements are communicated to and measured by the compression testing machine and the internal pressure and hoop strain on test cylinder 103 determined. The resultant hoop stress of test cylinder 103 is then calculated using a hoop stress equation. Hoop stress equations which are well known to those of skill in the art. In one embodiment, the hoop stress equation utilizes at least the hoop strain.

Referring now to FIGS. 11-16, another embodiment in accordance with the invention is illustrated in which expandable cylinder 108 of device 100 is formed of more than two wedges. In the present embodiment, eight (8) wedges 1102A-1102H are utilized rather than two wedges as earlier described with reference to wedges 105A and 105B and FIGS. 1-9.

When placed together each wedge 1102A-1102H forms a corresponding eighth of expandable cylinder 108. As earlier described, expandable cylinder 108 has a 360 degree external surface with cylindrical cross section, and has an internal upper cavity 114 and an internal lower cavity 116 which meet at a midline A. In one embodiment upper cavity 114 and lower cavity 116 are conically shaped as earlier described. In this embodiment, each wedge 1102A-1102H has a 45 degree exterior surface and has a shaped interior surface formed such that, when placed together, each wedge 1102A-1102H forms an eighth of upper cavity 114 and lower cavity 116. As earlier described, upper cavity 114 and lower cavity 116 each have a graduated conical shape with cylindrical cross section that decreases in diameter toward a midline A.

Figure 15:
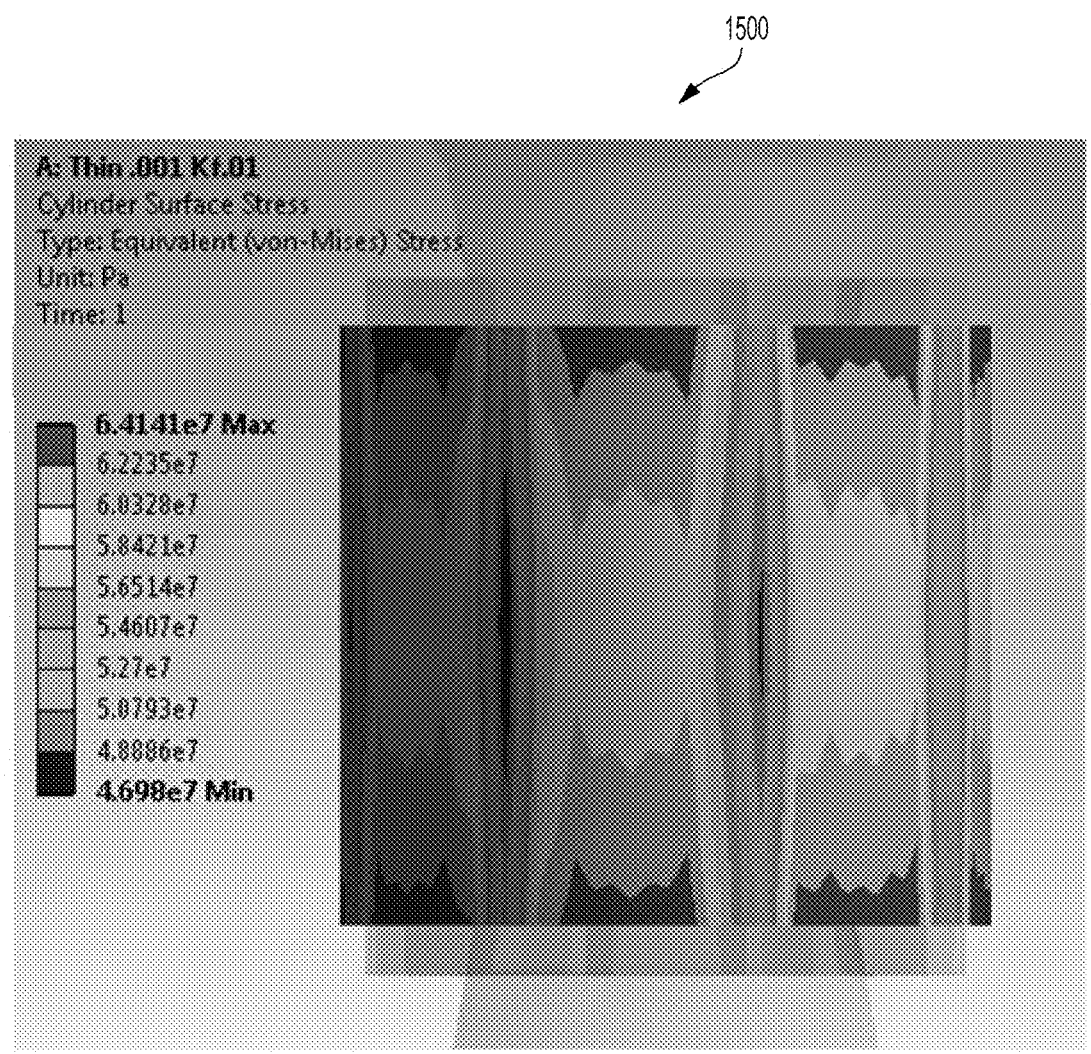
FIG. 15 illustrates an ANSYS computer model of cylinder surface stress on a test cylinder resulting from an internal pressure applied by the device of FIG. 11 in accordance with another embodiment of the invention.
Figure 16:
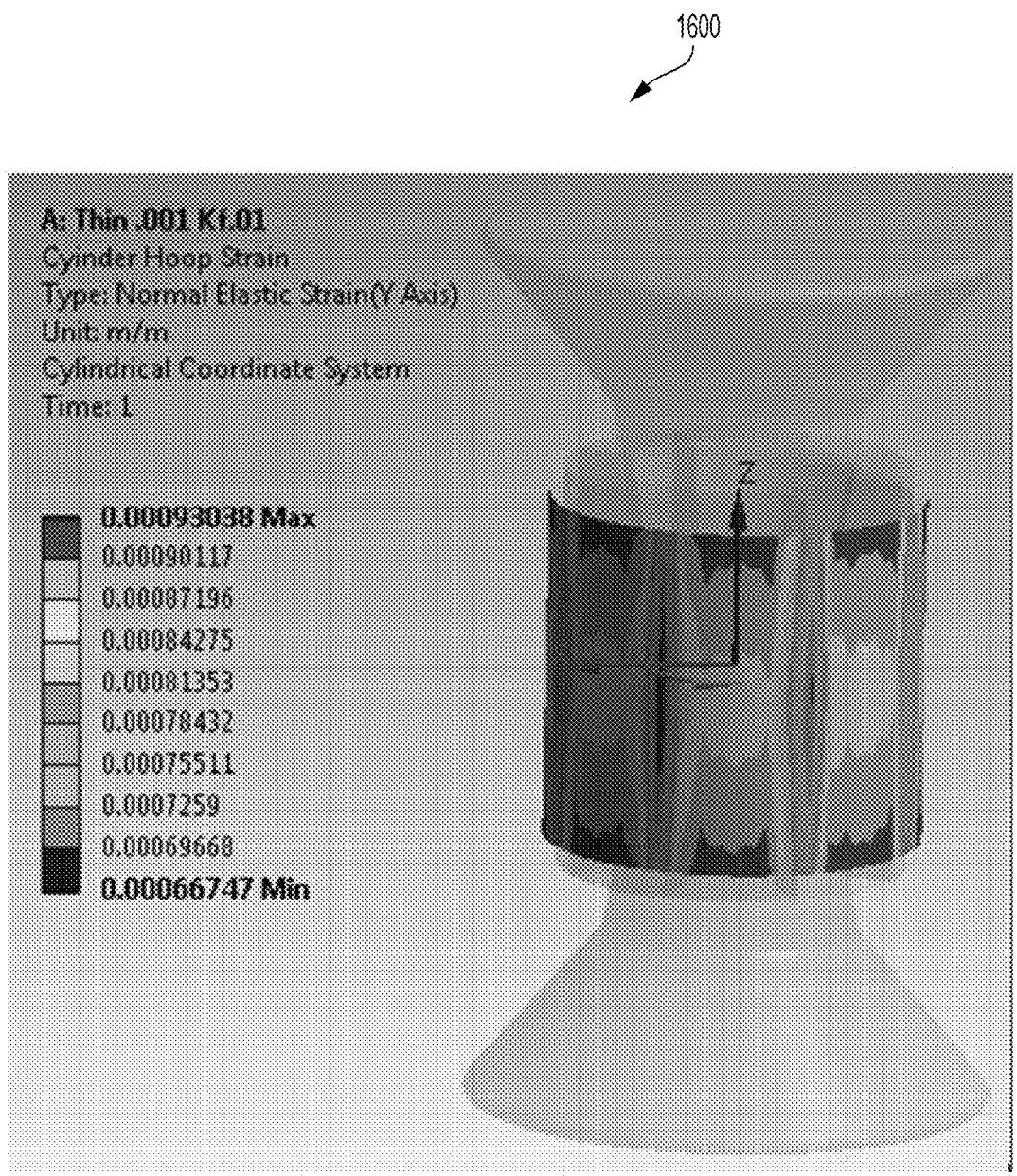
FIG. 16 illustrates an ANSYS computer model of hoop strain on a test cylinder resulting from an internal pressure applied by the device of FIG. 11 in accordance with one embodiment of the invention.

FIG. 15 illustrates an ANSYS (ANSYS, Inc. Canonsburg, Pa.) computer simulation model 1500 of cylinder surface stress on a test cylinder, such as test cylinder 103, resulting from an internal pressure applied by device 100 in the embodiment described with reference to FIGS. 11 and 14. FIG. 16 illustrates an ANSYS computer simulation model 1600 of hoop strain on a test cylinder, such as test cylinder 103, resulting from an internal pressure applied by device 100 in the embodiment described with reference to FIGS. 11 and 14.

The embodiments of FIGS. 11-16 can be utilized for determining an internal pressure and hoop stress of a hollow cylindrical object (e.g., test cylinder 103) when inserted into and connected with a compression testing machine in a process similar to that earlier described with reference to method 1000 and FIG. 10, and in which wedges 1102A-1102H are utilized to form expandable cylinder 108 rather than wedges 105A, 105B.

Embodiments in accordance with the invention reduce the time, expense, and danger inherent with the prior art systems which utilized a pressurized fluid for determining an internal pressure and hoop stress of a hollow cylindrical object. Embodiments in accordance with the invention have multiple potential applications, such in the testing of pressure vessels and pipes. The embodiments of the device described herein can be formed of various materials that are stiffer and stronger than the material(s) forming a cylinder to be tested, i.e., a test cylinder. In various embodiments, expandable cylinder 108, conical rams 101, 106 and shim 104 can be formed of the same or of different materials. In one embodiment, expandable cylinder 108 and conical rams 101, 106 are formed of 17-4 stainless steel in the annealed condition. In one embodiment, expandable cylinder 108, conical rams 101, 106, and shim 104 are formed of 17-4 stainless steel in the annealed condition.

This disclosure provides exemplary embodiments of the present invention. The scope of the present invention is not limited by these exemplary embodiments. Numerous variations, whether explicitly provided for by the specification or implied by the specification or not, may be implemented by one of skill in the art in view of this disclosure. In particular numbers of wedges may be utilized to form expandable cylinder 108 and the operations of method 100 are not limited to the order presented.

What is claimed is:

1. A device for applying internal pressure to a hollow cylindrical object comprising:
    an upper conical ram having a first guide hole centrally formed in a first facing surface;
    a lower conical ram having a second guide hole centrally formed in a second facing surface, wherein said second guide hole and said first guide hole are aligned to allow a guide rod to be positioned within both said first guide hole and said second guide hole;
    an expandable cylinder, said expandable cylinder having a 360 degree cylindrical exterior surface, an internal conical upper cavity shaped to receive at least a portion of said upper conical ram and an internal conical lower cavity shaped to receive at least a portion of said lower conical ram; and
    a guide rod positioned within at least a portion of said first guide hole and said second guide hole, said guide rod for aligning said upper conical ram and said lower conical ram.

2. The device of claim 1 wherein said upper conical ram further comprises a first tab; and
    wherein said lower conical arm further comprises a second tab.

3. The device of claim 2 wherein said first tab and said second tab are shaped to allow connection of said device to a compression testing machine.

4. The device of claim 1 wherein said device further comprises:
    a shim.

5. The device of claim 1 wherein said expandable cylinder comprises:
    a first wedge having a 180 degree exterior surface and an interior surface shaped to form one half of said upper cavity and one half of said lower cavity of said expandable cylinder; and
    a second wedge having a 180 degree exterior surface and an interior surface shaped to form a corresponding one half of said upper cavity and one half of said lower cavity of said expandable cylinder.

6. The device of claim 1 wherein said expandable cylinder comprises:
    a plurality of wedges, each wedge having an exterior surface that forms a portion of said 360 degree exterior surface of said expandable cylinder and having an interior surface shaped to form a portion of said upper cavity and at least a portion of said lower cavity of said expandable cylinder.

7. The device of claim 6 wherein said plurality of wedges comprises two wedges, each wedge having a 180 degree exterior surface and an interior surface shaped to form one half of said upper cavity and one half of said lower cavity of said expandable cylinder.

8. The device of claim 6 wherein said plurality of wedges comprises eight wedges, each wedge having a 45 degree exterior surface and an interior surface shaped to form one eighth of said upper cavity and one eighth of said lower cavity of said expandable cylinder.

9. A method for applying an internal pressure to a hollow cylindrical object comprising:
    obtaining a test cylinder;
    inserting an expandable cylinder into said test cylinder, said expandable cylinder having a 360 degree cylindrical exterior surface, an internal conical upper cavity shaped to receive at least a portion of an upper conical ram and an internal conical lower cavity shaped to receive at least a portion of a lower conical ram;
    inserting said lower conical ram from below said test cylinder at least partially into said lower cavity of said expandable cylinder, said lower conical ram having a second guide hole centrally formed on a second facing surface;
    inserting a guide rod from above said test cylinder into said second guide hole;
    inserting said upper conical ram from above said test cylinder at least partially into said upper cavity of said expandable cylinder, said upper conical ram having a first guide hole centrally formed on a first facing surface, wherein said first guide hole is aligned over said guide rod such that said guide rod passes into said first guide hole, and further wherein said first facing surface and said second facing surface are separated by a gap having a distance, d;
    applying a measured compressive force to said lower conical ram and said upper conical ram to cause said lower conical ram and said upper conical ram to move vertically toward a midline of said expandable cylinder and create an outward radial motion which applies an internal pressure and resultant hoop strain on said test cylinder; and
    determining a hoop stress of said test cylinder based on at least said hoop strain.

10. The method of claim 9 further comprising:
    inserting a shim between said exterior surface of said expandable cylinder and an interior surface of said test cylinder.

11. The method of claim 9 wherein said measured compressive force is applied by a compression testing machine, said compression testing machine for applying said measured compressive force applied to said upper and lower conical rams, and for measuring stress applied to said test cylinder from one or more stress sensors attached to said test cylinder from said compression testing machine.

12. The method of claim 11 wherein said compression testing machine is a uniaxial compression testing machine.

13. The method of claim 9 wherein said expandable cylinder comprises:
    a first wedge having a 180 degree exterior surface and an interior surface shaped to form one half of said upper cavity and one half of said lower cavity of said expandable cylinder; and
    a second wedge having a 180 degree exterior surface and an interior surface shaped to form a corresponding one half of said upper cavity and one half said lower cavity of said expandable cylinder.

14. The method of claim 9 wherein said expandable cylinder comprises:
   a plurality of wedges, each wedge having an exterior surface that forms a portion of said 360 degree exterior surface of said expandable cylinder and having an interior surface shaped to form a portion of said upper cavity and a portion of said lower cavity of said expandable cylinder.

15. The method of claim 14 wherein said plurality of wedges comprises two wedges, each wedge having a 180 degree exterior surface and an interior surface shaped to form one half of said upper cavity and one half of said lower cavity of said expandable cylinder.

16. The method of claim 14 wherein said plurality of wedges comprises eight wedges, each wedge having a 45 degree exterior surface and an interior surface shaped to form one eighth of said upper cavity and one eighth of said lower cavity of said expandable cylinder.

17. An expandable cylinder for use in applying an internal pressure to a hollow cylindrical object comprising:
   a plurality of wedges, each wedge having an exterior surface that forms a portion of a 360 degree exterior surface of said expandable cylinder and having an interior surface shaped to form a portion of an internal conical upper cavity and a portion of an internal conical lower cavity of said expandable cylinder.

18. The expandable cylinder of claim 17 wherein said plurality of wedges comprises two wedges, each wedge having a 180 degree exterior surface and an interior surface shaped to form one half of said upper cavity and one half of said lower cavity of said expandable cylinder.

19. The expandable cylinder of claim 17 wherein said plurality of wedges comprises eight wedges, each wedge having a 45 degree exterior surface and an interior surface shaped to form one eighth of said upper cavity and one eighth of said lower cavity of said expandable cylinder.

20. The expandable cylinder of claim 17 wherein said upper cavity is shaped to receive at least a portion of an upper conical ram and said lower cavity is shaped to receive at least a portion of a lower conical ram.

* * * * *